US011981662B2

(12) United States Patent
Aguilera et al.

(10) Patent No.: US 11,981,662 B2
(45) Date of Patent: May 14, 2024

(54) PYRAZOLE DERIVATIVES WITH ANTICANCER ACTIVITY

(71) Applicants: BOARD OF REGENTS, THE UNIVERSITY OF TEXAS SYSTEM, Austin, TX (US); THE REGENTS OF THE UNIVERSITY OF CALIFORNIA, Oakland, CA (US)

(72) Inventors: Renato J. Aguilera, El Paso, TX (US); Subhas S. Karki, El Paso, TX (US); Sujeet Kumar, El Paso, TX (US); Manuel L. Penichet, Los Angeles, CA (US)

(73) Assignees: BOARD OF REGENTS, THE UNIVERSITY OF TEXAS SYSTEM, Austin, TX (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/964,110

(22) Filed: Oct. 12, 2022

(65) Prior Publication Data
US 2023/0115335 A1    Apr. 13, 2023

Related U.S. Application Data

(60) Provisional application No. 63/254,899, filed on Oct. 12, 2021.

(51) Int. Cl.
| | | |
|---|---|---|
| *C07D 403/12* | (2006.01) |
| *A61K 31/416* | (2006.01) |
| *A61K 31/4192* | (2006.01) |
| *A61K 31/454* | (2006.01) |
| *A61K 31/5377* | (2006.01) |
| *A61K 45/06* | (2006.01) |
| *A61P 35/00* | (2006.01) |
| *A61P 35/02* | (2006.01) |
| *C07D 231/54* | (2006.01) |
| *C07D 405/14* | (2006.01) |

(52) U.S. Cl.
CPC .......... *C07D 403/12* (2013.01); *A61K 31/416* (2013.01); *A61K 31/4192* (2013.01); *A61K 31/454* (2013.01); *A61K 31/5377* (2013.01); *A61K 45/06* (2013.01); *A61P 35/00* (2018.01); *A61P 35/02* (2018.01); *C07D 231/54* (2013.01); *C07D 405/14* (2013.01)

(58) Field of Classification Search
CPC .. C07D 403/12; C07D 231/54; C07D 405/14; A61P 35/00; A61P 35/02; A61K 31/416; A61K 31/4192; A61K 31/454; A61K 31/5377; A61K 45/06
See application file for complete search history.

(56) References Cited

U.S. PATENT DOCUMENTS 9,828,342 B2 * 11/2017 Horne .................. C07D 209/38

FOREIGN PATENT DOCUMENTS

WO    WO-2013162469 A1 * 10/2013 .............. A61P 35/00

OTHER PUBLICATIONS

Ibrahim, H. S. et al. "Isatin-Pyrazole Benzenesulfonamide Hybrids Potently Inhibit Tumor-Associated Carbonic Anhydrase Isoforms IX and XII." European Journal of Medicinal Chemistry, vol. 103, (Sep. 16, 2015), pp. 583-593. (Year: 2015).*
Taher, A. T. et al. "Synthesis of Novel Isatin-Thiazoline and Isatin-Benzimidazole Conjugates as Anti-Breast Cancer Agents." Archives of pharmacal research, vol. 34, No. 10 (Oct. 2011), pp. 1615-1621. (Year: 2011).*
Gutierrez et al., Cell biology and toxicology 35, 503-519, 2019.
Lema et al., Current Cellular Biochemistry 1, 1-14, 2011.
Stathias et al., Nucleic Acids Research 2019.
Huang et al., Oncology reports 47, 2022.
Wu et al., Journal of cellular and molecular medicine 26, 3243-53, 2022.
Hu et al., European journal of medicinal chemistry 158, 884-95, 2018.
Gutierrez et al., Cells 11, 2022.

* cited by examiner

*Primary Examiner* — Jean P Cornet
*Assistant Examiner* — Chihyi Lee
(74) *Attorney, Agent, or Firm* — POLSINELLI PC

(57) ABSTRACT

The inventors have used a differential nuclear staining (DNS) assay to discover compounds with cytotoxic activity against the CEM cell line that has been determined to be highly sensitive to a variety of anti-cancer compounds. Compounds were synthesized based on a pyrazole backbone structure. Several newly synthesized compounds have been tested to identify the compounds with highest activity. One compound identified is the SSK-3 compound which has been tested on cancer cell lines and determined that it induced apoptosis via phosphatidylserine membrane exposure and activation of caspase 3 in the CEM lymphoma cell line.

4 Claims, 3 Drawing Sheets

| Drug name | Description | median | Target |
|---|---|---|---|
| niclosamide | DNA replication inhibitor, STAT inhibitor | | STAT3 |
| rottlerin | large conductance potassium channel activator, MAP kinase inhibitor, PKC inhibitor | 100.00 | KCNF2, PRKCD, TGM2 |
| VU0418946-1 | hypoxia inducible factor activator | 100.00 | HIF1A |
| SA-1478098 | metalloprotease inhibitor | 100.00 | MMP12, MMP14, MMP2, MMP9, MMP9 |
| rhodomyrtoxin-b | cytotoxic, DNA intercalator | 99.99 | |
| BRD-K7261D817 | apoptosis, protein inhibitor | 99.99 | |
| VU0418947-2 | hypoxia inducible factor activator | 99.99 | |
| cyclosporin-a | calcineurin inhibitor, cyclophilin inhibitor, immunosuppressant, insulin expre... | 99.99 | PPIA, ABCB11, CAMLG, CYP3A5, CYP3A7, PPIF, PPIC |
| tunicamycin | GLCNAC phosphotransferase inhibitor | 99.99 | GNPTAB |
| hikizimycin | antibiotic, bacterial RNA synthesis inhibitor | 99.98 | |
| IKK-2-inhibitor-V | IKK inhibitor, NFkB pathway inhibitor, protein kinase inhibitor | 99.98 | IKBKB |
| perflundol | dopamine receptor antagonist, serotonin receptor agonist, T-type calcium channel blocker | 99.98 | CACNA1G, DRD1, DRD2 |
| JTC-801 | opioid receptor antagonist | 99.98 | OPRL1 |
| SCH-79797 | protease activated receptor antagonist | 99.98 | F2R |
| 5-nonyloxytryptamine | serotonin receptor agonist | 99.98 | HTR1B, HTR1D |
| tegaserod | serotonin receptor partial agonist, serotonin receptor agonist | 99.98 | HTR4, HTR1B, HTR2A, HTR2C |
| TW-37 | BCL inhibitor, MCL1 inhibitor | 99.98 | BCL2, BCL2L1, MCL1 |
| NNC-55-0396 | T-type calcium channel blocker | 99.98 | CATSPER1, CATSPER2, CATSPER3, CATSPER4 |
| puromycin | adrenergic receptor agonist, protein synthesis inhibitor | 99.97 | NHP2L1, RPL10L, RPL11, RPL13A, RPL15, RPL19, RPL... |
| suloctidil | adrenergic receptor antagonist, platelet aggregation inhibitor, vasodilator | 99.97 | |
| clotrimazolium | calcium channel blocker, calmodulin antagonist | 99.97 | ATP2B1, PDE1A |
| CGP-71683 | neuropeptide receptor antagonist | 99.97 | NPY5R |
| PAC-1 | ATPase inhibitor | 99.97 | ATP2A1 |
| cyclopiazonic-acid | caspase activator | 99.96 | CASP3 |
| azaciditine | DNA methyltransferase inhibitor, antimetabolite, DNA methylase inhibitor, DNA... | 99.96 | DNMT1 |
| lasalocid | ionophore antibiotic | 99.96 | |
| dacosoporin | photoactivated to produce toxic reactive oxygen species, PKC inhibitor | 99.96 | |
| CGK-733 | ATM kinase inhibitor, ATR kinase inhibitor | 99.96 | ATM, ATR |
| cucurbitacin-I | inhibitor of STAT3/JAK2 signaling, JAK inhibitor, lipocortin synthesis stimulator | 99.96 | JAK2, STAT3 |
| AG-1478 | protein tyrosine kinase inhibitor, tyrosine kinase inhibitor | 99.96 | EGFR |
| WAY-170523 | metalloproteinase inhibitor | 99.96 | MMP13 |
| brefeldin-a | antibiotic that disrupts Golgi function, brefeldin A inhibited guanine nucleotide... | 99.95 | ARF1, ARFGEF1, ARFGEF2, CYTH2, GBF1, SAR1A |
| phorbol-12-myristate | GABA receptor agonist, acetylcholine receptor allosteric modulator, GABA... | 99.95 | CHRNA7, GABRB3, GLRA3, P2RX7 |
| FCCP | PKC activator, CD antagonist | 99.95 | CD4, KCNT2, PRKCA, TRPV4 |
| GW-406833 | mitochondrial oxidative phosphorylation uncoupler | 99.95 | CNR2 |
| PAC-1 | cannabinoid receptor agonist | 99.95 | CASP3 |
| | caspase activator | | |

FIG. 4

PYRAZOLE DERIVATIVES WITH ANTICANCER ACTIVITY

PRIORITY

This application claims priority to U.S. Provisional patent Ser. No. 63/254,899 filed Oct. 12, 2021, which is incorporated herein by reference in its entirety.

STATEMENT REGARDING FEDERALLY FUNDED RESEARCH

This invention was made with government support under GM103713 and MD007592 awarded by the National Institutes of Health; and 2U54MD007592 awarded by the National Institute on Minority Health and Health Disparities (NIMHD). The government has certain rights in the invention.

BACKGROUND

The present invention is directed to compositions and methods for treating cancer patients. Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult.

Thus, there is a need for more effective treatment regimens for patients with anti-cancer therapies, whether used as single agents or combined with other agents.

SUMMARY

The inventors have used a DNS assay to discover compounds with cytotoxic activity against the CEM cell line that has been determined to be highly sensitive to a variety of anti-cancer compounds. Compounds were synthesized based on a pyrazole backbone structure. Several newly synthesized compounds have been tested to identify the compounds with highest activity. One compound identified is the SSK-3 compound which has been tested on cancer cell lines (see Table 2) and determined that it induced apoptosis via mitochondrial depolarization and phosphatidylserine membrane exposure in the HL-60 leukemia cell line.

Certain embodiments are directed to SSK-3 compound, its derivatives, and methods for using the same in the treatment of cancer. The SSK-3 compound has the following chemical structure:

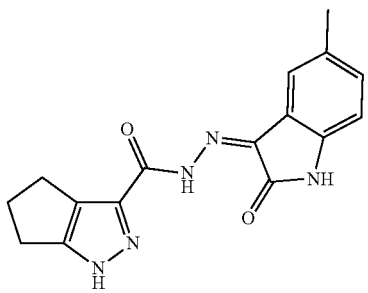

Other aspects of the invention are directed to pharmaceutical compositions comprising a compound of SSK-3 or a derivative as described below as Formula I, Formula II, and Formula III.

Certain embodiments are directed to methods of treating a subject with cancer comprising administering to the subject a compound as described herein. The subject can have lymphoma, leukemia, myeloma, prostate cancer, melanoma, lung cancer, colon cancer, breast cancer, or liver cancer. In certain aspects the method further comprises administering a second anti-cancer agent in combination with a compound described herein.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 4. Comparison of the DEGs in common between SSK-3 and P3C treatments to those in the LINCS database. Heat map indicates similar expression patterns in the nine distinct cell lines in the database. The known activities (Description) and potential molecular targets (Targets) are indicated. Note that the higher the median level, the higher the match to the gene signatures within the LINCS database.

DESCRIPTION

Figure 1:
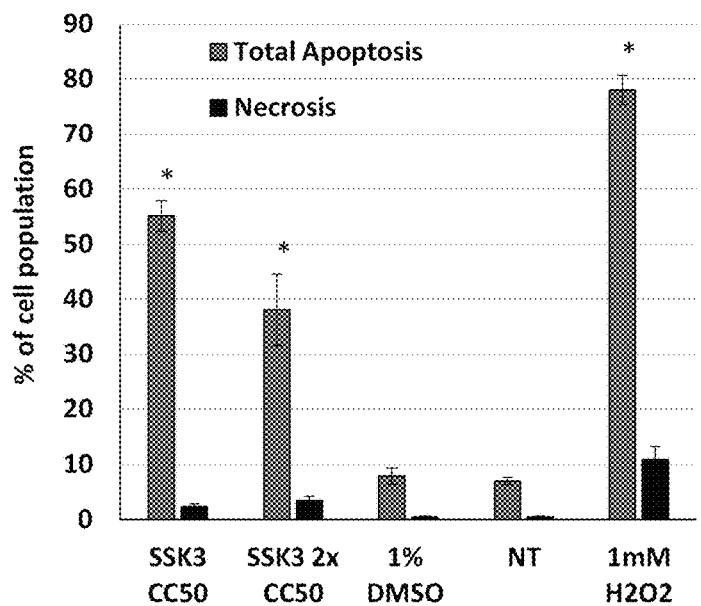
FIG. 1. Induction of Phosphatidylserine (PS) externalization by SSK-3 compounds. CEM cells were treated at the CC50 and twice (2×) that concentration of SSK-3. Note that PS externalization is an early marker of apoptosis. * Indicates P value less than 0.001.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain embodiments are directed to a compound and compositions containing SSK-3 having the chemical structure of:

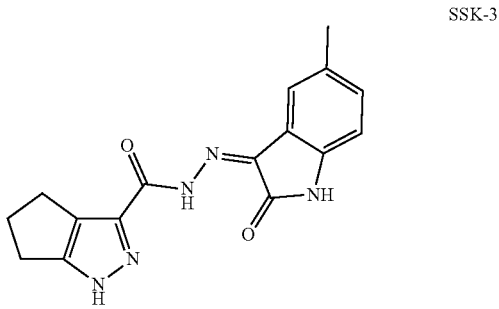 [SMILES: Cc1ccc2c(c1)/C(=N/NC(=O)c1n[nH]c3c1CCC3)C(=O)N2]

SSK-3

SSK-3 can be formulated in pharmaceutical composition. In certain aspects the SSK-3 composition can be administered to a subject in need treatment for cancer.

In certain aspects, a compound has the chemical formula of Formula I

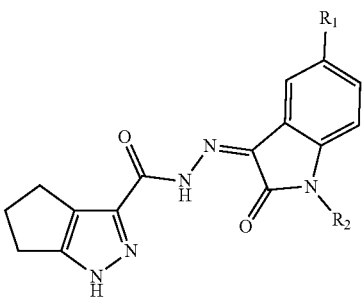

Formula I wherein $R_1$ and $R_2$ are independently selected from hydrogen, halogen, fluorine (F), chlorine (Cl), bromine (Br), iodine (I), C1 to C3 alkyl, aryl, cycloakyl, heterocycle, C1 substituted cyclohexyl, or C1 substituted heterocyclohexyl. In certain aspects $R_1$ selected from hydrogen, halogen, fluorine (F), chlorine (Cl), bromine (Br), iodine (I), or C1 to C3 alkyl, and $R_2$ is selected from hydrogen, C1 to C3 alkyl, phenyl, C1 substituted cyclohexyl, or C1 substituted heterocyclohexyl. In certain aspects the heterocylohexyl is a morpholine or piperidine.

In certain aspects, a compound has the chemical formula of Formula II

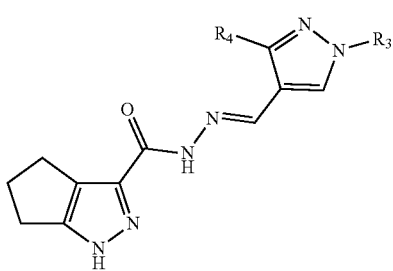

Formula II wherein $R_3$ and $R_4$ are independently selected from cycloalkyl, aryl, heteroaryl, heterocycle, or polycyclic. In certain aspects $R_3$ and $R_4$ are independently phenyl or substituted phenyl. The substituted phenyl can have a substituent selected from C1 to C3 alkyl, alkoxy, or halogen. In certain aspects the polycyclic is benzopyran (e.g., coumarin).

In certain aspects, a compound has the chemical formula of Formula III

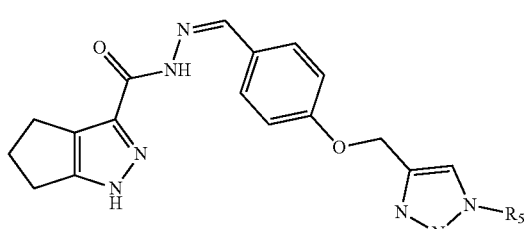

Formula III wherein $R_5$ is selected from phenyl, substituted phenyl, cycloalkyl, or a heterocycle. In certain aspects the substitute phenyl is substituted with an —$NO_2$, —F, —Cl, —Br, —I, —SH, —CN, —$N_3$, or —OH.

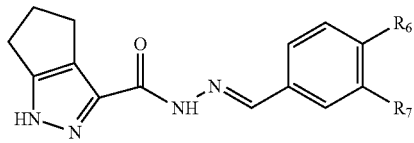

Formula IV

Certain aspects are directed to a compound of Formula IV wherein $R_6$ and $R_7$ are independently selected from hydrogen, hydroxy, halogen, fluorine (F), chlorine (Cl), bromine (Br), iodine (I), C1 to C3 alkyl, methoxy, ethoxy, propoxy, aryl, cycloakyl, heterocycle, C1 substituted cyclohexyl, or C1 substituted heterocyclohexyl. In certain aspects $R_6$ selected from hydrogen, halogen, fluorine (F), chlorine (Cl), bromine (Br), iodine (I), or C1 to C3 alkyl, and $R_7$ is selected from hydrogen, hydroxy, C1 to C3 alkyl, methoxy, ethoxy, propoxy, phenyl, C1 substituted cyclohexyl, or C1 substituted heterocyclohexyl. In certain aspects $R_b$ is a halogen (e.g., Br) or alkoxy (e.g., methoxy) and $R_7$ is hydrogen or hydroxy.

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

As used herein, the term "nitro" means —$NO_2$; the term "halo" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$(Me), —$CH_2CH_3$(Et), —$CH_2CH_2CH_3$(n-Pr), —$CH(CH_3)_2$(iso-Pr), —$CH_2CH_2CH_2CH_3$ (n-Bu), —$CH(CH_3)CH_2CH_3$ (sec-butyl), —$CH_2CH(CH_3)_2$(iso-butyl), —$C(CH_3)_3$(tert-butyl), —$CH_2C(CH_3)_3$(neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl).

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S(O$_2$)—R', where R' is an alkyl group. R' may have a specified number of carbons (e.g. "C$_{1-4}$alkylsulfonyl").

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

I. Compositions and Methods for Treating Cancer

Compositions according to aspects of the present invention prevent and inhibit cancer cell multiplication and tumor development and are considered useful as chemotherapeutic and chemopreventive agents. Methods including administration of composition comprising compound described herein to a subject in need thereof are provided.

A. Compositions and Pharmaceutical Compositions

Certain aspects relate to compositions including compounds of SSK-3, Formula I, Formula II, or Formula III as described herein. Compositions and pharmaceutical compositions including compounds described herein may be provided as a pharmaceutically acceptable salt, hydrate, amide or ester according to aspects of the present invention.

Pharmaceutical compositions include compounds described herein and a pharmaceutically acceptable carrier. The term "pharmaceutically acceptable carrier" refers to a carrier which is substantially non-toxic to a subject to which the composition is administered and which is substantially chemically inert with respect to the active component or components. A pharmaceutical composition according to the invention generally includes about 0.1-99% of a compound described herein.

Pharmaceutical compositions of compounds described herein are suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included. Such formulations are administered by a suitable route including parenteral and oral administration. Administration may include systemic or local injection, and particularly intravenous injection.

These compositions may also contain excipients such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more anti-cancer compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent. Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Pharmaceutically acceptable carriers and formulation of pharmaceutical compositions are known in the art, illustratively including, but not limited to, as described in Remington: The Science and Practice of Pharmacy, 21-Ed., Lippincott, Williams & Wilkins, Philadelphia, Pa., 2006; and Allen, L. V. et al., Ansel's Pharmaceutical Dosage Forms and Drug Delivery Systems, $8^{th}$Ed., Lippincott, Williams & Wilkins, Philadelphia, Pa., 2005.

Compositions described herein can be use in treatment of a subject having cancer or at risk of having cancer, such as skin cancer and other cancers including, but not limited to, hematological cancers and cancers of the liver, prostate, breast, brain, stomach, pancreas, blood cells, uterus, cervix, ovary, lung, colon, connective tissues (sarcomas) and other soft tissues. Non-limiting examples of hematologic cancers include leukemia, lymphoma, and myeloma, such as: multiple myeloma (MM); active multiple myeloma; smoldering multiple myeloma; plasmacytoma; solitary plasmacytoma of the bone; extramedullary plasmacytoma; light chain myeloma; non-secretory myeloma; immunoglobulin G (IgG) myeloma; immunoglobulin A (IgA) myeloma; immunoglobulin M (IgM) myeloma; immunoglobulin D (IgD) myeloma; immunoglobulin E (IgE) myeloma; hyperdiploid multiple myeloma; non-hyperdiploid multiple myeloma; Hodgkin lymphoma; non-Hodgkin lymphoma; acute lymphoblastic leukemia; acute myeloid leukemia; essential thrombocythemia; polycythemia vera; primary myelofibrosis; systemic mastocytosis; chronic myeloid leukemia; chronic neutrophilic leukemia; chronic eosinophilic leukemia; refractory anemia with ringed sideroblasts; refractory cytopenia with multilineage dysplasia; refractory anemia with excess blasts type 1; refractory anemia with excess blasts type 2; myelodysplastic syndrome (MDS) with isolated del (5q); MDS unclassifiable; chronic myelomonocytic leukemia (CML); atypical chronic myeloid leukemia; juvenile myelomonocytic leukemia; myeloproliferative/myelodysplastic syndromesunclassifiable; B lymphoblastic leukemial/lymphoma; T lymphoblastic leukemial/lymphoma; diffuse large B-cell lymphoma; primary central nervous system lymphoma; primary mediastinal B-cell lymphoma; Burkitt lymphoma/leukemia; follicular lymphoma; chronic lymphocytic leukemia (CLL)/small lymphocytic lymphoma; B-cell prolymphocytic leukemia; lymphoplasmacytic lymphoma/Waldenstrom macroglobulinemia; Mantle cell lymphoma; marginal zone lymphomas; post-transplant lymphoproliferative disorders; HIV-associated lymphomas; primary effusion lymphoma; intravascular large B-cell lymphoma; primary cutaneous primary cutaneous B-cell lymphoma; hairy cell leukemia; monoclonal gammopathy of unknown significance; Anaplastic large cell lymphoma, Angioimmunoblastic T-cell lymphoma, Hepatosplenic T-cell lymphoma, B-cell lymphoma, reticuloendotheliosis, reticulosis, Mucosa-associated lymphatic tissue lymphoma, B-cell chronic lymphocytic leukemia, Waldenstrom's macroglobulinemia, Lymphomatoid granulomatosis, Nodular lymphocyte predominant Hodgkin's lymphoma, plasma cell leukemia, Acute erythraemia and erythroleukaemia, Acute erythremic myelosis, Acute erythroid leukemia, Heilmeyer-SchOner disease, Acute megakaryoblastic leukemia, Mast cell leukemia, Panmyelosis, Acute panmyelosis with myelofibrosis, Lymphosarcoma cell leukemia, Stem cell leukemia, Chronic leukaemia of unspecified cell type, Subacute leukaemia of unspecified cell type, Accelerated phase chronic myelogenous leukemia, Acute promyelocytic leukemia, Acute basophilic leukemia, Acute eosinophilic leukemia, Acute monocytic leukemia, Acute myeloblastic leukemia with maturation, Acute myeloid dendritic cell leukemia, Adult T-cell leukemiallymphoma, Aggressive NK-cell leukemia, B-cell chronic lymphocytic leukemia, B-cell leukemia, Chronic myelogenous leukemia, Chronic idiopathic myelofibrosis, Kahler's disease, Myelomatosis, Solitary myeloma, Plasma cell leukemia, Angiocentric immunoproliferative lesion, Lymphoid granulomatosis, Angioimmunoblastic lymphadenopathy, T-gamma lymphoproliferative disease, Waldenstrom's macroglobulinaemia, Alpha heavy chain disease, Gamma heavy chain disease, and Franklin's disease. In some embodiments, the hematological cancer is lymphoma, leukemia, or multiple myeloma.

Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of a composition administered is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to an inventive composition, a therapeutically effective amount of a composition is effective to ameliorate or prevent one or more signs and/or symptoms of the condition. For example, a therapeutically effective amount of a composition including a compound described herein is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an inventive composition.

Methods of treating a subject are provided according to aspects of the present invention which include administering a therapeutically effective amount of a composition as described herein to a subject in need thereof, wherein the subject has an abnormal proliferative condition, such as cancer, pre-neoplastic hyperproliferation, cancer in-situ, neoplasms, metastasis, tumor or benign growth. Subjects are identified as having, or at risk of having, cancer using well-known medical and diagnostic techniques.

The term "subject" refers to an individual in need of treatment for a pathological condition responsive to the beneficial effects of compositions of the present invention, particularly cancer. While the present invention describes compositions and methods for treatment of human subjects in need thereof, the present invention is not limited to human subjects and the term subject generally includes mammals and birds, such as, but not limited to, non-human primates, cats, dogs, cows, horses, rodents, pigs, sheep, goats and poultry.

Methods of treatment include administration of a therapeutic composition described herein to a subject having skin cancer or at risk of having skin cancer, including basal cell carcinoma, squamous cell carcinoma and malignant melanoma.

Methods of treatment include administration a therapeutic composition described herein to a subject having cancer or at risk of having cancer, such as, but not limited to, cancers of the liver, prostate, breast, brain, stomach, pancreas, blood cells, uterus, cervix, ovary, lung, colon, connective tissues (sarcomas) and other soft tissues.

A therapeutically effective amount of composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

B. Combination Treatments

Combinations of therapeutic agents are administered according to aspects of the present invention. In some respects, a compound described herein and at least one additional therapeutic agent are administered to a subject to treat cancer in a subject in need thereof. In still further aspects, a compound as described herein and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

According to aspects of the present invention, combination therapies include: (1) administration of pharmaceutical compositions that include a compound described herein in combination with one or more additional therapeutic agents; or (2) co-administration of compound described herein with one or more additional therapeutic agents wherein the one or more additional therapeutic agents are formulated in the same or a different composition. When using separate formulations, agents may be administered at the same time or at different times; and two or more therapeutic agents may be administered at the same time or at different times with reference to the other therapeutic agents.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

II. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in, the specific embodiments which are disclosed and still obtain a like or similar result without departing from the spirit and scope of the invention.

Example 1

Pyrazole Derivatives with Anticancer Activity

Figure 5:
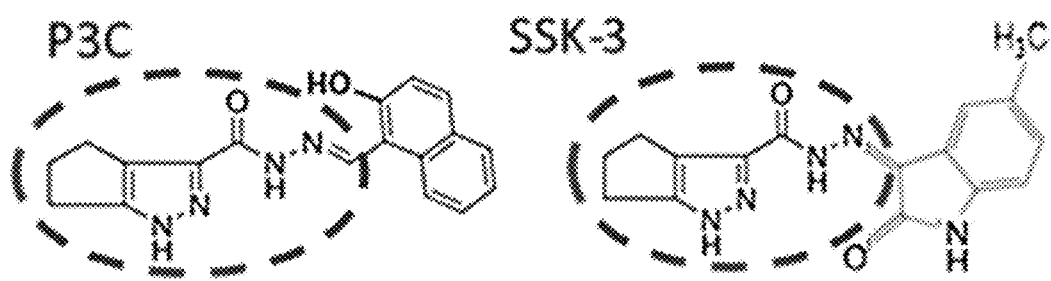
FIG. 5. Structures of two similar pyrazole compounds. P3C(N'-[(2-hydroxy-1-naphthyl)methylene]-1,4,5,6-tetrahydrocyclopenta[c]pyrazole-3-carbohydrazide) was the original compound identified while SSK-3 (N-(5-methyl-2-oxoindolin-3ylidene)-1,4,5,6-tetrahydrocyclopenta[c]pyrazole-3-carbohydrazide) was subsequently synthesized with the intention of obtaining a more potent cytotoxic analogue. The area encircled is the backbone that appears to confer the cytotoxic activity.

Using the high throughput Differential Nuclear Staining (DNS) screening assay (Lema et al., Current Cellular Biochemistry 1, 1-14, 2011) 15 pyrazole compounds were synthesized and screened on the human T-cell Acute Lymphoblastic Leukemia CEM cell line (Tables 1 and 2). The Cytotoxic Concentration that results in 50% cell death ($CC_{50}$) was determined for each of the new compounds (in μM concentrations) and compound SSK-3 was found to have significant activity. The compounds were synthesized based on a pyrazole backbone structure previously determined to have potent cytotoxic activity (FIG. 5). Several commercial and non-commercial analogues (see Table 3) have been tested and determined that the ones with highest activity have a similar structure circled in FIG. 5. Of all the compounds tested, the most active compound was a pyrazole-3-carbohydrazide compound (P3C) that exhibited cytotoxic activity on several cancer cell lines with low $CC_{50}$ values and low activity against the non-cancerous line Hs-27. SSK-3 has been tested on a few cancer cell lines (see Table 4) and also found to induce programmed cell death via a variety of biochemical assays. It is interesting to note that SSK-3 exhibited more activity on lymphoma/leukemia cell lines (Table 4) than on adherent cancer cell lines. Since the non-adherent (free floating) lymphoma/leukemia cell lines divide faster than the adherent cell lines, they were incubated for a shorter period (48 h) of time with the compound. When compared with the non-cancerous "normal" HS-27 human fibroblast cell line, it is clear that SSK-3 was more selective as it was 37 times more cytotoxic toward the T-cell lymphoma cell line Jurkat (CC50 0.42 μM) than HS27 (CC50=15.4 μM; Table 4).

TABLE 1
Structuers of synthesized pyrazole compounds.
| Name SSK- | Structure |
|---|---|
| 1 | 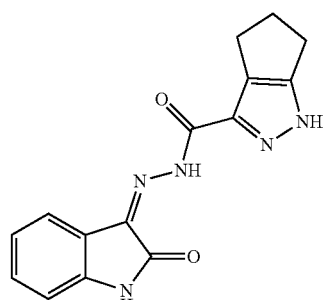 |
| 2 | 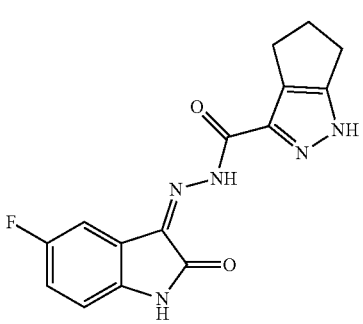 [SMILES: O=C1Nc2ccc(F)cc2/C1=N/NC(=O)c1n[nH]c2c1CCC2] |
| 4 | 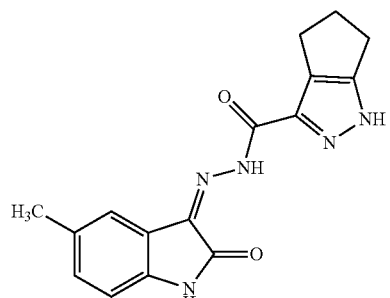 |
| 5 | 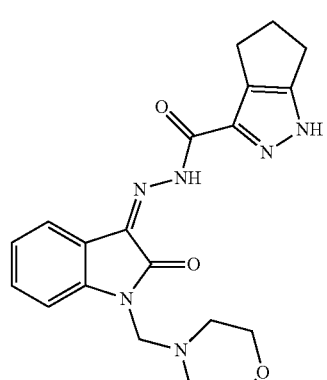 |

TABLE 1-continued

Structuers of synthesized pyrazole compounds.

| Name SSK- | Structure |
|---|---|
| 6 | *(structure: cyclopenta-fused pyrazole-3-carbohydrazide linked via N–NH–N= to a 3-oxoindolin-2-ylidene bearing an N-(piperidin-1-ylmethyl) substituent)* |
| 7 | *(structure: cyclopenta-fused pyrazole-3-carbohydrazide linked via HN–N=CH to 1,3-diphenyl-1H-pyrazol-4-yl)* |
| 8 | *(structure: cyclopenta-fused pyrazole-3-carbohydrazide linked via HN–N=CH to 3-(4-methylphenyl)-1-phenyl-1H-pyrazol-4-yl)* |
| 9 | *(structure: cyclopenta-fused pyrazole-3-carbohydrazide linked via HN–N=CH to 3-(4-nitrophenyl)-1-phenyl-1H-pyrazol-4-yl)* |

TABLE 1-continued
Structuers of synthesized pyrazole compounds.
Name
SSK-  Structure
10
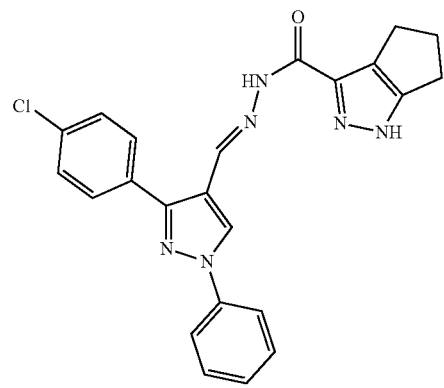 [SMILES: O=C(N/N=C/c1cn(-c2ccccc2)nc1-c1ccc(Cl)cc1)c1n[nH]c2c1CCC2]
11
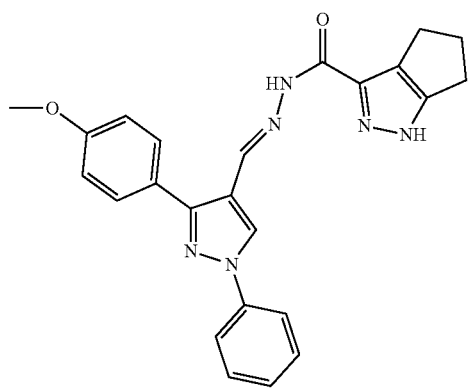 [SMILES: COc1ccc(-c2nn(-c3ccccc3)cc2/C=N/NC(=O)c2n[nH]c3c2CCC3)cc1]
12
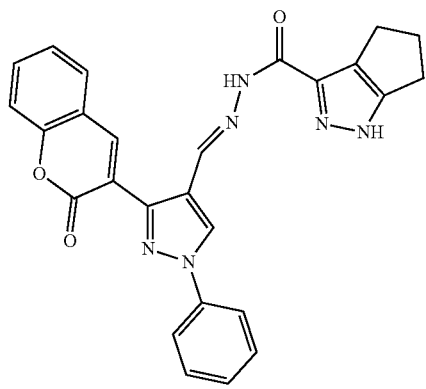 [SMILES: O=C(N/N=C/c1cn(-c2ccccc2)nc1-c1cc2ccccc2oc1=O)c1n[nH]c2c1CCC2]
13
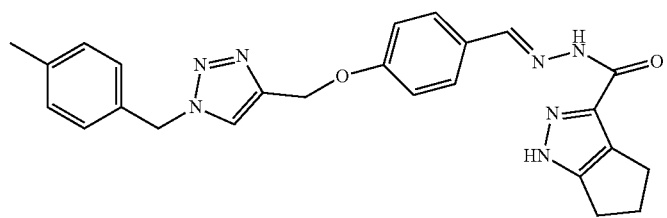 [SMILES: Cc1ccc(Cn2cc(COc3ccc(/C=N/NC(=O)c4n[nH]c5c4CCC5)cc3)nn2)cc1]

TABLE 1-continued

Structures of synthesized pyrazole compounds.

| Name SSK- | Structure |
|---|---|
| 14 | (structure) |
| 15 | (structure) |

TABLE 2

Initial Screen.

| Name | CEM CC$_{50}$ |
|---|---|
| SSK-1 | 12.08 ± 1.11 |
| SSK-2 | >10 |
| SSK-3 | 1.39 ± 0.68 |
| SSK-4 | 5.023 ± 0.78 |
| SSK-5 | >10 |
| SSK-6 | >10 |
| SSK-7 | 8.15 ± 0.23 |
| SSK-8 | 3.60 ± 0.16 |
| SSK-9 | Insoluble |
| SSK-10 | 7.83 ± 0.13 |
| SSK-11 | 3.14 ± 0.33 |
| SSK-12 | 8.25 ± 0.26 |
| SSK-13 | >10 |
| SSK-14 | >10 |
| SSK-15 | >10 |

TABLE 3

Additional Pyrazole compounds tested.

| Compound | | Cell Line CC$_{50}$ (μM) | | | |
|---|---|---|---|---|---|
| Name | Structure | CEM | MDA-MD-231* | MCF10A* | HS-27* |
| P3C | (structure) | 0.48 +/− 0.02 | 0.49 +/− 0.12 | 0.86 +/− 0.07 | 3.47 +/− 0.45 |
| P3C.1 | (structure) | 0.07 +/− 0.01 | 0.097 +/− 0.01 | 0.42 +/− 0.03 | 0.78 +/− 0.02 |

TABLE 3-continued

Additional Pyrazole compounds tested.

| Compound | | Cell Line CC$_{50}$ (μM) | | | |
|---|---|---|---|---|---|
| Name | Structure | CEM | MDA-MD-231* | MCF10A* | HS-27* |
| P3C.2 | | 0.12 +/- 0.013 | 1.83 +/- 0.17 | 0.53 +/- 0.04 | 4.1 +/- 1.26 |
| P3C.3 | | 0.72 +/- 0.04 | 1.61 +/- 0.17 | 2.16 +/- 0.04 | >10 |
| P3C.4 | | 0.56 +/- 0.05 | 2.91 +/- 0.33 | 2.46 +/- 0.05 | >10 |
| P3C.5 | | >10 | 9.88 +/- 0.43 | 6.36 +/- 0.29 | >10 |
| P3C.6 | | 3.31 +/- 0.78 | 2.53 +/- 0.48 | 5.85 +/- 0.40 | 9.94 +/- 1.32 |
| P3C.7 | | 10.32‡ | >7.5 | >7.5 | >20 |

TABLE 3-continued

Additional Pyrazole compounds tested.

| Compound | | Cell Line CC$_{50}$ (µM) | | | |
|---|---|---|---|---|---|
| Name | Structure | CEM | MDA-MD-231* | MCF10A* | HS-27* |
| P3C.8 | | 2.13 | 7.21 | 7.67 | >10 |
| P3C.9 | | 0.81 +/− 0.01 | 1.49 +/− 0.41 | 0.80 +/− 0.09 | >10 |
| P3C.10 | | 0.56 +/− 0.06 | 2.91 +/− 0.33 | 2.46 +/− 0.05 | >10 |
| CV-1** | | 2.87 +/− 0.43‡ | 7.59 +/− 0.85 | 7.42 +/− 0.09 | >10 |
| CV-2** | | 3.04 +/− 0.44‡ | >7.5 | >7.5 | >10 |
| CV-3** | | >5‡ | 6.69 +/− 0.255 | 5.95 +/− 0.1 | >10 |

*72 hr incubations.
**Compounds synthesized at UTEP

TABLE 4

CC$_{50}$ (µM) values of SSK-3 activity on several cell lines.

| Tissue Origin | Cell Line | SSK-3 |
|---|---|---|
| Lymphoma-Leukemia* | CEM | 1.4 +/− 0.68 |
| | RAMOS | 1.65 +/− 0.11 |
| | HL-60 | 0.75 +/− 0.19 |
| | Jurkat | 0.42 +/− 0.01 |
| | NALM-6 | 2.035 +/− 0.035 |
| | K562 | 2.13 +/− 0.52 |
| Mantle cell Lymphoma | MiNO | 1.07 +/− 0.188 |
| | Jeko-1 | 1.24 +/− 0.29 |
| | Z138 | 3.36 +/− 0.21 |
| | JVM-2 | 0.79 +/− 0.15 |
| | JVM-13 | 0.79 +/− 0.019 |
| Multiple Myeloma | MM.1S | 4.61 +/− 0.28 |
| | MM.1R | 3.88 +/− 0.46 |
| | U226 | 4.44 +/− 0.47 |
| | RPMI-8226 | 2.47 +/− 0.145 |
| Breat Cancer | MDA-MB231 | 2.3 +/− 0.03 |
| | MDA-468 | 3.98 +/− 0.25 |
| | HCC1419 | >20 |
| | T47D | 3.87 +/− 0.34 |

TABLE 4-continued $CC_{50}$ (μM) values of SSK-3 activity on several cell lines.

| Tissue Origin | Cell Line | SSK-3 |
| --- | --- | --- |
| Pancreatic cancer | PANC-1 | 1.86 +/− 0.12 |
| Colon Cancer | Colo 205 | 2.43 +/− 0.18 |
| Normal Fibroblast | HS27 | 15.4 +/− 0.66 |

*Lymphoma leukemia cell lines were treated for 48 hrs -the rest 72 hrs

The data indicate that the novel pyrazole derivatives can be used as therapeutic agents for incurable hematopoietic malignancies such as multiple myeloma (MM), a plasma cell malignancy, and mantle cell lymphoma (MCL), a B-cell non-Hodgkin lymphoma (NHL). Novel drugs such as SSK-3 and its pyrazole derivatives can potentially be used alone or in combination with known anticancer drugs or immunotherapeutic agents to treat these hematological cancers.

Additional pyrazole compounds were purchased or synthesized to determine if more active compounds could be detected and to determine the part of the structure that was most important for activity (e.g., Table 3). Analysis of other analogues revealed that there are more active compounds such as P3C, P3C.1, P3C.6, and P3C.10 that show varying amounts of cytotoxicity against the non-cancerous MCF-10A and HS-27 cell lines tested. Of the recently synthesized compounds, only SSK-3 (Tables 1 and 4) exhibited significant activity below 2 μM. Interestingly, SSK-3 exhibited the strongest activity against the Jurkat cell line ($CC_{50}$=0.42 μM). Two other pyrazole compounds P3C and P3C.1 also exhibited strong activity against this cell line than toward CEM with $CC_{50}$ values of 0.37 and 0.39 μM, respectively. These compounds were tested in mice at a concentration of 160 mg/kg and after 3-4 daily doses, animals tolerated the treatments well. Different cytotoxicity patterns of the compounds against distinct cell lines has been noted, and it is therefore possible that distinct pyrazoles will act on distinct cellular effectors with different modes of action. However, all of the pyrazole compounds so far tested including SSK-3 induce cell death via the intrinsic apoptosis pathway as will be described below.

SSK-3 has potent cytotoxic activity against a panel of human cancer cell lines. The cytotoxic activity of SSK-3 was examined by the DNS assay (Lema et al., *Current Cellular Biochemistry* 1, 1-14, 2011). Lymphoma/leukemia cell lines, which grow in suspension, were incubated for 48 h with the compounds. Since the adherent cells generally divide at a slower rate than the non-adherent cell lines, the MDA-MB231, HCC1419, T47D, COLO205, PANC-1, A-549 adherent cancer cells lines were incubated for 72 h in the presence of the compounds. After treatment, images were acquired and analyzed to determine percentages of live/dead cells and their cytotoxicity. The $CC_{50}$ values (concentration of compound resulting in 50% cell death) ranged from 0.0.42 μM to >20 μM, corresponding to the Jurkat and the breast carcinoma HCC1419 cell lines, respectively (Table 2). The Hs-27 non-cancerous human foreskin fibroblast cell line was used for comparison purposes. The $CC_{50}$ values obtained with the Hs-27 cell line ($CC_{50}$ of 15.4 μM) indicates that it is more resistant to SSK-3 treatment than the lymphoma cell lines (Table 2).

SSK-3 induces significant phosphatidylserine externalization. To corrobotate whether SSK-3 utilizes apoptosis to induce cell death, we measured phosphatidylserine (PS) externalization in SSK-3-treated CEM cells by using the Annexin V-FITC/PI assay (3, 4). For these experiments, two concentrations of SSK-3 were used, 0.24 μM ($CC_{50}$) and 0.48 μM (2×$CC_{50}$). The results indicate that SSK-3 induces significant PS externalization in a dose-response manner, as compared to solvent control (FIG. 1). As expected, the $H_2O_2$ positive control for death caused the highest percentage of PS externalization (~78%), whereas DMSO-treated and untreated cells showed low levels of PS externalization <10%; FIG. 1). These findings suggest that SSK-3 induces PS externalization, a biochemical hallmark of apoptosis.

Figures 2A, 2B, 2C:
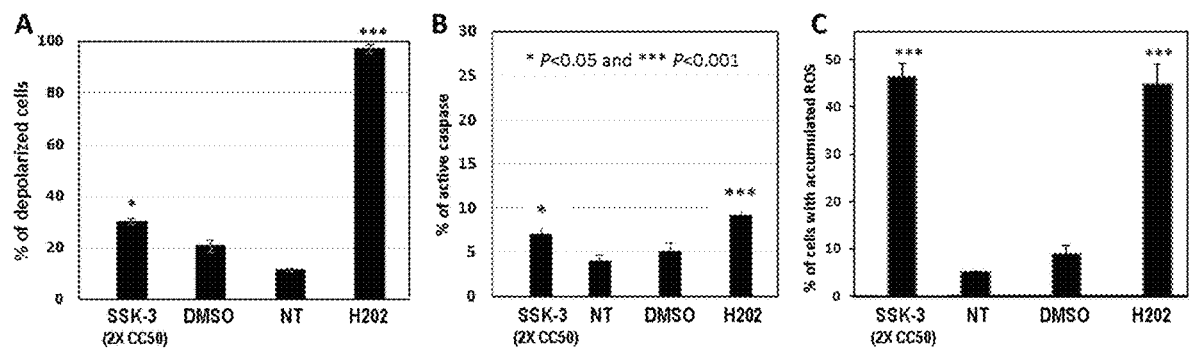
FIG. 2A-2C. SSK-3 induces the intrinsic apoptosis pathway. CEM cells were treated at the $CC_{50}$ and twice (2×) that concentration of SSK-3. (A) Mitochondrial depolarization was observed after SSK-3 treatment. (B) Activation of Caspase 3 was detected via flow cytometry (Gutierrez et al., *Cell biology and toxicology* 35, 503-519, 2019). (C) Generation of Reactive Oxygen Species by SSK-3 treatment was detected as previously described (Gutierrez et al., *Cell biology and toxicology* 35, 503-519, 2019). * Indicates P value less than 0.01 while *** indicates a P value of 0.001.
Figure 3:
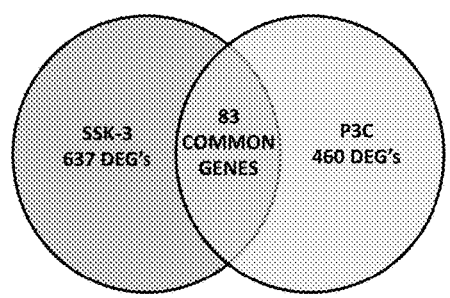
FIG. 3. Transcriptome analysis of breast cancer (MDA-MB-231) cells treated for 6 hours with the $CC_{50}$ values of SSK-3 and P3C. Note that both compounds affected the expression of greater than 400 genes. The large number of genes affected by either compound may indicate that they activate distinct pathways to elicit cell death.

SSK-3 induces caspase-3 activation. Mitochondrial depolarization is one of the salient features of cell-death induction and this was observed after treatment of CEM cells with SSK-3 (FIG. 2A). To further support and extend the findings that suggest that SSK-3 induces apoptosis, caspase-3 activation was measured in cells exposed to SSK-3. CEM cells were treated with SSK-3 for 7 h and subsequently stained with the NucView caspase-3 substrate and analyzed via flow cytometry (Gutierrez et al., *Cell biology and toxicology* 35, 503-19, 2019) (FIG. 2B). As expected, SSK-3 treatment in CEM cells induced a statistically significant activation of caspase-3 ($P<0.05$; FIG. 3) when compared to the DMSO control. These results provide further support that SSK-3 induces cell death via apoptosis. As shown in FIG. 2C, SSK-3 treatment also led to the generation of Reactive Oxygen Species (ROS) which is also a biochemical feature of apoptosis. Apart from the biochemical assays that indicate induction of apoptosis, treatment with SSK-3 for 2 hours also led to severe disruption of membrane microtubule organization as compared to the DMSO control. Although not shown, SSK-3 and P3C also cause cell cycle arrest and interfere with cellular replication.

Transcriptome analysis of genes affected by other Pyrazole compounds. Gene expression analysis of cancer cells treated with SSK-3 and P3C was performed to determine if the treated cells exhibit a similar expression pattern. The MDA-MD-231 breast cancer cell line was selected for further analyses to compare the pyrazole-induced gene expression profile with available databases of gene expression profiles of drug treated cells. Although each compound affected more than 400 differentially expressed genes (DEGs) in treated cells, only 83 genes were found in common (FIG. 3). Of these DEGs, 64 genes were found to be upregulated while 15 DEGs were downregulated by greater than 2-fold. The genes in common are predicted to be involved in cell-death induction while the other genes may result in minor cytotoxic differences between the compounds.

As shown in FIG. 4, the inventors compared the 83 genes in common to the gene signatures of the NIH Library of Integrated Network-Based Cellular Signatures (LINCS) database that contain the expression profiles of human cancer cells treated with thousands of drugs and other perturbagens (Stathias et al., *Nucleic Acids Research* 2019). This library contains the data of gene expression profiles of 9 cell lines representing prostate (PC3 and VCAP), melanoma (A375), lung (A549 and HCC515), immortalized embryonic kidney cells (HA1E), colon (HT29), breast (MCF-7), and liver (HEPG2) cell lines. The top 3 matches (100) were with niclosamide, rottlerin, and VU-0418946-1. Nicosamide is an oral anti-helminthic drug that is FDA approved to treat tapeworm infections and recently shown to have anti-cancer activity though apoptosis (Huang et al., *Oncology reports* 47, 2022). It is mode of action is complex as it has been linked to inhibition of Wnt/β-catenin, mTOR and STAT3 signaling pathways (Arend et al., *Oncotarget* 7, 86803-15, 2016). In addition, this drug has been shown to inhibit proliferation by inhibiting CREB-dependent signaling pathways (Chae et al., *Oncotarget* 9, 4301-17, 2018). Rottlerin is a natural product with a complex pharmacological profile and is described as an inhibitor protein kinase C (PKC) (Wu et al., *Journal of cellular and molecular medicine* 26, 3243-53, 2022). It has been recently described that factors that induce hypoxia like VU-0418946-1 and VU-0418947-2 can mediate proteasome inhibition and be potent anti-cancer agents (Hu et al., *European journal of* medicinal chemistry 158, 884-95, 2018). Overall, protein kinase inhibitors and hypoxia inducible factor activators and were the top two classes of perturbagens that were over-represented in the comparison to the LINCs database. Recent work has revealed that P3C treatment led to dephosphorylation of important signal transduction molecules including CREB, p38, ERK, STAT3, and Fyn. In addition, P3C caused hyperphosphorylation of JNK and NF-κB in breast cancer cells, an indication that both the p38MAPK/STAT3 and ERK1/2/CREB signaling pathways were negatively affected (Gutierrez et al., Cells 11, 2022). Recent biochemical assays, indicate that P3C acts as a Tubulin polymerization inhibitor, and this could be one of the pathways used by the pyrazoles to destabilize cell membranes and induce cell death.

In conclusion, the data indicate that SSK-3 can induce cell death via separate pathways that involve important signal-transduction pathways and directly affect cellular structure by inhibiting tubulin polymerization.

Example 2

Preparation of N-(5-Methyl-2-Oxoindolin-3Ylidene)-1,4,5,6-Tetrahydrocyclopenta [C]Pyrazole-3-Carbohydrazide (SSK-03)

In a round flask, 1,4,5,6-tetrahydrocyclopenta[c]pyrazole-3-carbohydrazide 166 mg (0.001 M), 5-methylindolin-2,3-dione 160 mg (0.001M), ethyl alcohol (20 ml) and glacial acetic acid (2 drops) were heated to reflux on water bath. Then cooled the contents of the reaction mixture, filtered the solid product and purified with dimethyl formamide and alcohol (8:2).

Yield: 80%; MP: 302° C. (decompose); FTIR (KBr cm-1): 3264, 3137, 2987, 2965, 2923, 1697, 1488, 1151. NMR (DMSO-d6): 13.92 (s, 1H, NH), 13.15 (s, 1H, NH), 11.12 (s, 1H, NH), 7.42 (s, 1H, ar), 7.20 (m, 1H, ar), 6.85 (m, 1H, ar), 2.79-2.67 (m, 6H, pyrazole), 2.32 (s, 3H, —CH3).

The invention claimed is:
1. A compound having the chemical structure of SSK3

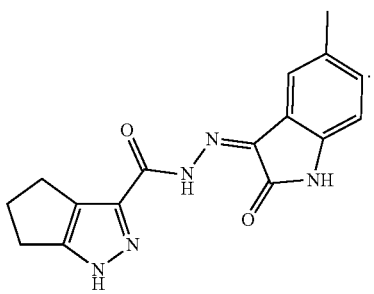

SSK-3

2. A pharmaceutical composition comprising a compound having the chemical structure of SSK3

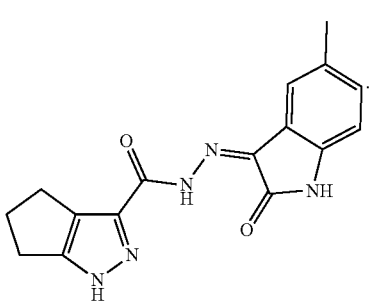

SSK-3

3. A method of treating a subject having a cancer comprising administering to the subject a compound having the chemical structure of SSK3

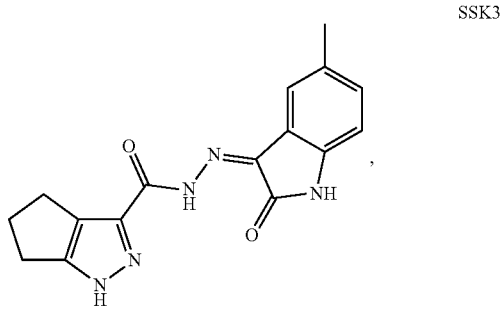 [SMILES: Cc1ccc2c(c1)/C(=N/NC(=O)c1n[nH]c3c1CCC3)C(=O)N2 ; ","]

SSK3 wherein the cancer is selected from the group consisting of hematological cancer, prostate cancer, melanoma, lung cancer, colon cancer, breast cancer, or liver cancer.
4. The method of claim 3, further comprising administering a second anti-cancer agent.

* * * * *